(12) United States Patent
Lucas (10) Patent No.: US 11,268,062 B2
(45) Date of Patent: Mar. 8, 2022

(54) WHOLE STILLAGE SEPARATION

(71) Applicant: LucasE3, L.C., Shawnee, KS (US)

(72) Inventor: Scott A Lucas, Shawnee, KS (US)

(73) Assignee: LucasE3, L.C., Shawnee, KS (US)

( * ) Notice: Subject to any disclaimer, the term of this patent is extended or adjusted under 35 U.S.C. 154(b) by 0 days.

(21) Appl. No.: 16/903,068

(22) Filed: Jun. 16, 2020

(65) Prior Publication Data

US 2020/0332246 A1  Oct. 22, 2020

Related U.S. Application Data

(62) Division of application No. 15/417,784, filed on Jan. 27, 2017, now Pat. No. 10,683,479.

(60) Provisional application No. 62/287,660, filed on Jan. 27, 2016.

(51) Int. Cl.
| | |
|---|---|
| *C12M 1/00* | (2006.01) |
| *C12M 1/26* | (2006.01) |
| *C12P 19/14* | (2006.01) |
| *B01D 11/04* | (2006.01) |
| *C12F 3/10* | (2006.01) |
| *C12P 7/06* | (2006.01) |

(52) U.S. Cl.
CPC ......... *C12M 47/00* (2013.01); *B01D 11/0446* (2013.01); *C12F 3/10* (2013.01); *C12M 21/12* (2013.01); *C12M 33/22* (2013.01); *C12M 47/08* (2013.01); *C12M 47/10* (2013.01); *C12M 47/20* (2013.01); *C12P 19/14* (2013.01); *C12P 7/06* (2013.01); *C12P 2203/00* (2013.01); *Y02E 50/10* (2013.01)

(58) Field of Classification Search
CPC ...... C12M 47/00; C12M 21/12; C12M 33/22; C12M 47/08; C12M 47/10; C12M 47/20; C12M 29/06; B01D 11/0446; C12F 3/10; C12P 19/14; C12P 7/06; C12P 2203/00; Y02E 50/10
See application file for complete search history.

(56) References Cited

U.S. PATENT DOCUMENTS

| | | | |
|---|---|---|---|
| 2,958,142 | A | 11/1960 | Kershaw et al. |
| 3,363,340 | A | 1/1968 | McKinley |
| 3,673,705 | A | 7/1972 | Wright et al. |
| 4,309,254 | A | 1/1982 | Dahlstrom |
| 5,178,543 | A | 1/1993 | Semans et al. |

(Continued)

FOREIGN PATENT DOCUMENTS

AU    2007303117    4/2008

OTHER PUBLICATIONS

Katzen, et al., "Ethanol Distillation: the Fundamentals", 1999, 270-273.

*Primary Examiner* — Rosanne Kosson
*Assistant Examiner* — Trevor Logan Kane
(74) *Attorney, Agent, or Firm* — Law Office of Mark Brown, LLC; Mark E. Brown (57) ABSTRACT

Spent stillage remaining after the fermentation of a feedstock for ethanol production may be processed to recover, use, and/or recycle the constituent components of the stillage. Stillage may be mixed, heated, and held at a desired temperature for a period of time. The stillage may then be cooled and treated with an enzyme. The enzymatically treated stillage may be emulsified with oil and water, and then permitted to settle into discrete layers. Individual layers may then be processed.

12 Claims, 5 Drawing Sheets

(56) References Cited

U.S. PATENT DOCUMENTS

| | | | |
|---|---|---|---|
| 5,354,203 A | 10/1994 | Kotch et al. | |
| 7,504,546 B2 | 3/2009 | Brown et al. | |
| 7,867,365 B2 | 1/2011 | Brown | |
| 7,988,580 B2 | 8/2011 | McCrary | |
| 8,173,412 B2 | 5/2012 | Dale | |
| 9,029,126 B2 * | 5/2015 | Bleyer | C12P 7/06 435/262 |
| 9,308,489 B2 | 4/2016 | Brown et al. | |
| 9,931,582 B2 | 4/2018 | Furlong | |
| 2009/0171724 A1 | 7/2009 | Allin et al. | |
| 2014/0053829 A1 * | 2/2014 | Lee | C13K 13/007 127/42 |
| 2014/0238881 A1 | 8/2014 | Stuhlmann et al. | |
| 2014/0343259 A1 | 11/2014 | Bleyer et al. | |
| 2015/0041305 A1 | 2/2015 | Overheul et al. | |
| 2015/0045594 A1 | 2/2015 | Overheul et al. | |
| 2016/0279560 A1 | 9/2016 | Furlong | |
| 2018/0290073 A1 | 10/2018 | Brown et al. | |
| 2019/0233354 A1 | 8/2019 | Lucas | |
| 2020/0171404 A1 | 6/2020 | Lucas | |

\* cited by examiner

WHOLE STILLAGE SEPARATION

CROSS-REFERENCE TO RELATED APPLICATIONS

This application is a Divisional of and claims priority in U.S. Non-Provisional patent application Ser. No. 15/417,784, filed Jan. 27, 2017, which claims priority in U.S. Provisional Patent Application No. 62/287,660, filed on Jan. 27, 2016, which is incorporated herein by reference.

FIELD OF INVENTION

The present invention relates to ethanol distillation. More particularly, the present invention relates to processing the stillage remaining after the formation process of ethanol production is completed.

BACKGROUND AND DESCRIPTION OF THE RELATED ART

Ethanol has become an increasingly popular fuel source. Because ethanol can be produced from a variety of plant sources, it is a renewable energy source with positive effects on the environment relative to petroleum-based fuels. Ethanol may be produced from a variety of inputs, but a common feedstock used for ethanol production within the United States is grain. Currently available ethanol is typically made from grain(s) such as corn, wheat, barley, soybeans, milo, and other grains. Such potential inputs into the ethanol production process are available in abundance in the United States. While providing environmental advantages over petroleum-based fuels, ethanol fuels still possess many of the advantages of petroleum-based fuels, such as the ability to power appropriately configured internal combustion engines and to be distributed in a liquid form.

SUMMARY OF THE INVENTION

Ethanol has become popular both as a basis for fuel and as an additive to petroleum based fuels because of these various benefits. Despite its popularity, however, ethanol production can suffer from waste, as only a small portion of the feedstock used in ethanol production is converted to fuel, leaving other potentially useful and valuable components of the feedstock unused. This problem may be particularly acute for grain-based ethanol, as the grains used as a feedstock for ethanol production typically have useful components other than the starches that are fermented to form the ethanol. Ethanol production may involve brewing, which is the fermentation of the sugars and/or starches present in a feedstock into alcohol using one or more variety of yeast. The feedstock may be processed, often by grinding or crushing the grain and then mixing the resulting material with water and yeast at a desired temperature(s) for a desired amount of time to facilitate the fermentation process. Spent stillage may comprise the materials remaining after alcohol from fermentation has been decanted. Spent stillage may contain proteins, oils, fibers, and/or other components of grain that are not readily fermentable. Systems and methods in accordance with the present invention permit the spent stillage to be separated into one or more constituent component to facilitate further processing of that component(s) for eventual use.

The present invention enables the spent stillage remaining after the fermentation step of ethanol production to be more fully utilized. Systems and methods in accordance with the present invention may be used to treat the stillage remaining after fermentation to separate the valuable components that remain and to fully utilize those components. In particular examples, by using high shear mixing to create an emulsion formed from the stillage product, vegetable oil, and water, the processing of the stillage into its constituent components may be facilitated. The emulsion may be allowed to settle into strata based upon the relative density of the components, permitting a desired component to be removed from the settling tank for additional processing to a desired end-product. Separating the components of the emulsion that settle into different layers permits materials to be separated for optimal processing into potentially valuable product streams.

Systems and methods in accordance with the present invention may further improve the environmental benefit of ethanol production by more fully utilizing the inputs used to produce ethanol, while also improving the economic profitability of ethanol production by creating additional products of value from the unfermented stillage remaining after brewing. The present invention enables the spent stillage remaining after the fermentation of a feedstock for ethanol production to be processed to recover, use, and/or recycle the constituent components of the stillage. In accordance with some examples in accordance with the present invention, stillage may be mixed, heated, and held at a desired temperature for a period of time. The stillage may then be cooled and treated with an enzyme. The enzymatically treated stillage may next be emulsified with oil and water, and then permitted to settle into discrete layers. Individual layers may then be processed. For example, a bottom layer may comprise fibers, a middle layer may comprise dissolved solids, and a top layer may comprise a mixture of oil and protein. Each of these layers may be processed in accordance with the present invention for a use such as, but not limited to, livestock feed, industrial inputs, and/or use in other aspects of ethanol production.

In some examples, the present invention comprises systems for processing spent stillage remaining after the fermentation process of ethanol production has concluded. A system in accordance with the present invention may comprise a high shear mixer that combines stillage from an ethanol fermenter with water and oil to create an emulsion. A system in accordance with the present invention may further comprise a settling tank that receives the emulsion of stillage, oil, and water and retains the emulsion for a predetermined period of time, thereby permitting components of the emulsion to separate into layers. A system in accordance with the present invention may further comprise at least one extraction mechanism that draws individual layers from the settling tank for further processing.

In further examples in accordance with the present invention, a system may comprise a vessel that receives spent stillage, that mixes the spent stillage, and that optionally heats the spent stillage to a first predetermined temperature. The vessel may retain the spent stillage at the first predetermined temperature for a first period of time. A system in accordance with the present invention may further optionally comprise a cooling chamber that rapidly cools the spent stillage after the spent stillage has been heated to the first predetermined temperature by the vessel. Such an exemplary system may further optionally comprise enzymatic treatment system that adds an enzyme to the spent stillage after it has been cooled in the cooling chamber and an emulsifier that mixes the spent stillage and the enzyme with oil and water to create an emulsion. A system in accordance with the present invention may further comprise a settling tank that receives the emulsion and retains the emulsion for a predetermined period of time to permit the emulsion to separate into layers. The layers formed in the settling tank may correspond to constituent components of the spent stillage, each of which may be useful or valuable for a different purpose but each of which may require different processing in order to be utilized. Accordingly, a system in accordance with the present invention may further comprise at least one system that withdraws individual layer(s) from the settling tank and may further comprise at least one system that processes at least one layer formed while the emulsion is held in the settling tank.

In other examples in accordance with the present invention, methods for processing spent stillage remaining after the fermentation process of ethanol production are provided. Such an exemplary method may optionally comprise heating the spent stillage to a first temperature and holding the spent stillage at the first temperature for a first period of time. Such an exemplary method may further optionally comprise flash cooling the spent stillage to a second temperature after the first period of time and, after the spent stillage has been cooled to the second temperature, optionally treating the spent stillage with an enzyme. The enzyme used to treat the spent stillage may comprise any enzyme that facilitates the chemical breakdown of the spent stillage, such as but not limited to alpha amylase. A method in accordance with the present invention may further comprise creating an emulsion combining the spent stillage with oil and water after the spent stillage has been treated with an enzyme. Such an emulsion may be formed through high shear mixing, such as may be achieved using a hydroheater. After forming an emulsion, a method in accordance with the present invention may comprise settling the emulsion of spent stillage, oil, and water at least until stratification of components of the emulsion into distinct layers occurs. After settling, a method in accordance with the present invention may comprise withdrawing distinct layers of the stratified emulsion for processing, such that different layers of the emulsion are processed in different ways.

Systems and methods in accordance with the present invention may isolate and concentrate a number of materials or products from the spent stillage of ethanol production. While the precise amounts and types of material that can be recovered in accordance with the present invention will vary based upon factors such as the type(s) of grain or other material used as a feedstock and the completeness of fermentation, the present invention may permit the production of approximately 1.2 pounds of corn of per bushel of input, 2.0 pounds of 50% protein per bushel of input, 8.0 pounds of fiber per bushel of input, and 4.0 pounds of feed syrup (a molasses substitute for use in animal feed) per bushel of input. While the economic value of such materials obtained using systems and methods in accordance with the present invention will necessarily depend upon market conditions, these materials would in many cases constitute waste products or low value composite material without the use of the current invention.

Systems and methods in accordance with the present invention are not limited to the use of any particular type of grain(s) as the feedstock used in ethanol production process, although the types and relative amounts of concentrated materials obtained from spent stillage in accordance with present invention may be expected to differ based upon the seedstock(s) used. Examples of types of grain that may be used as ethanol seedstock in accordance with the present invention include, but not limited to, corn, milo, wheat, and/or barley. Further, the materials isolated and/or concentrated using systems and methods in accordance with the present invention may be further processed in a variety of ways and may be used for any purpose.

BRIEF DESCRIPTION OF THE SEVERAL VIEWS OF THE DRAWINGS

Examples of systems and methods in accordance with the present invention are described in conjunction with the attached drawings, wherein.

DETAILED DESCRIPTION

Systems and methods in accordance with the present invention facilitate the separation of spent stillage remaining after the fermentation process of ethanol production has concluded into constituent component parts for further processing. Such processing may separate the spent stillage into component parts such as protein, oil, fibers, residual dissolved solids, some remaining unfermented starches that may be concentrated or processed for further use.

Figure 1:
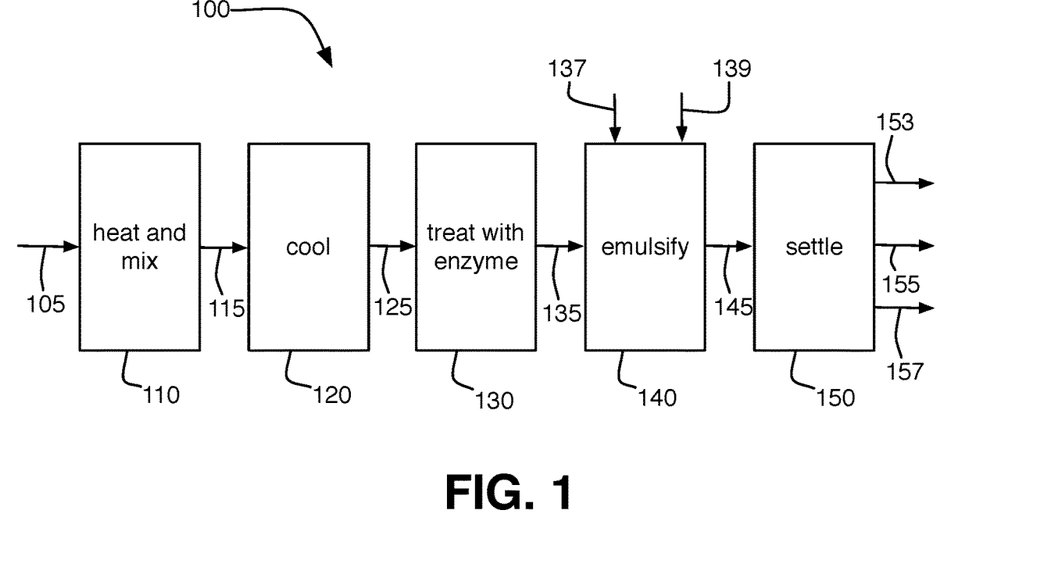
FIG. 1 schematically illustrates an example of a method in accordance with the present invention.

Referring now to FIG. 1, an example of a systems and methods in accordance with the present invention is illustrated. A method 100 for processing whole stillage in accordance with the present invention may receive 105 spent stillage after brewing has completed. Brewing refers to the fermentation of the sugars and/or starches of stillage into alcohol by yeast. Spent stillage may comprise the materials remaining after alcohol from fermentation has been decanted. Stillage input 105 may contain water, flour and other remnants of the grain that was processed (typically by grinding or crushing) to facilitate the fermentation process. The stillage input 105 may possess a number of constituent components derived from the grain, such as protein, oil, fibers, residual dissolved solids, some remaining unfermented starches, and the like, possibly as well as residual water and a small amount of alcohol.

The stillage 105 may be heated and mixed in step 110. Step 110 may be performed, for example, using a hydroheater or other similar device to introduce steam for purposes of heating the stillage. Step 110 may then hold the stillage at a desired temperature in a vessel for a desired amount of time to enable the stillage to begin to be broken down through chemical and physical processes. For example, the heated stillage may be held at a temperature of approximately 250° F. for approximately five minutes. In some examples, the temperature attained in step 110 may comprise a first temperature and the time at which the stillage is held at the first temperature may comprise a first period of time. In some examples, step 110 may only mix the stillage, rather than both heating and mixing the stillage.

The mixture may be transferred for cooling step 120. Cooling step 120 may use, for example, a vacuum chamber that performs flash cooling of the mixture. Cooling step 120 may enable vapors released by the rapidly cooling mixture to be withdrawn for further use within the system or elsewhere, such as to heat evaporative systems elsewhere in an ethanol production facility. Cooling step 120 may reduce the stillage mixture to a temperature of approximately 185° F., which may comprise a second temperature.

The cooled stillage mixture may optionally proceed to an enzymatic treatment step 130 to mix one or more enzyme with the stillage to further facilitate the chemical and physical breakdown of the stillage as part of a method in accordance with the present invention to separate the stillage into constituent components. Enzymatic treatment step 130 may comprise adding one or more enzyme to the stillage and mixing the enzyme with the stillage. One example of an enzyme that is appropriate for treatment to facilitate the separation of components remaining in the stillage for further processing is alpha amylase, although other enzymes may be used for this purpose, and various enzymes may be preferable depending upon the types of grain used for the ethanol production. In some examples of methods and systems in accordance with the present invention, the enzymatic treatment step may be omitted.

After enzymatic treatment 130 (if used), the stillage may be moved for emulsification step 140. The stillage may be emulsified 140 through the addition of water 137 and vegetable oil 139 in conjunction with high shear mixing to create and emulsion of the treated stillage with the added water and oil. High shear mixing may be performed using, for example, a hydroheater. In addition to or instead of mixing water and oil with the stillage to form an emulsion, an emulsion may be formed using air or other types of liquid(s) mixed with the stillage at a high shear force.

The emulsion may be allowed to settle in step 150. Settling step 150 may occur in the same vessel in which the emulsion was created, although in other examples the emulsification process may deposit the emulsion directly or indirectly into a settling tank. The emulsion may be allowed to settle for a predetermined period of time, such as one to three hours. In some examples, the settling time may comprise an hour and a half. Settling may result in the physical separation of the contents of the emulsion, which may then be removed individually from the settling tank. For example, a top layer may be removed 153, a middle layer may be removed 155, and a bottom layer may be removed 157. The top layer, middle layer, and bottom layer may comprise different components of the stillage that have been chemically and physically broken down and then isolated from other components for more efficient processing than would be possible without the emulsification and settling steps. The top layer may comprise vegetable oil, protein, and/or water in varying amounts. The middle layer may comprise various dissolved solids. The bottom layer may comprise fiber. More or fewer layers may be separated in the settling step 150 than the three illustrated in the example of FIG. 1.

While systems and methods in accordance with the present invention are generally described with regard to FIG. 1, various aspects of example components of such a system and method are described in further detail below. The present invention is not limited to any of the particular examples described herein, which are provided for exemplary and explanatory purposes only.

Figure 2:
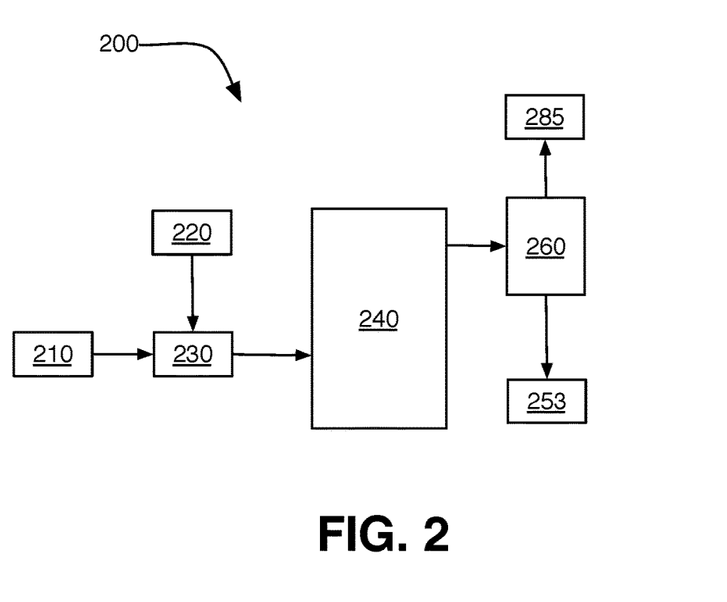
FIG. 2 schematically illustrates an example of a portion of an exemplary system in accordance with the present invention for initially mixing, heating, and cooling stillage.

FIG. 2 illustrates an example of a portion of an exemplary system 200 in accordance with the present invention for initially mixing, heating, and cooling stillage. Beer stillage bottoms 210 may comprise the spent stillage remaining after fermentation has concluded. Stillage bottoms 210 may be combined with high velocity steam 220 using a hydroheater 230 to produce heated and well-mixed stillage for further processing in accordance with the present invention. The hydroheater 230 may heat the stillage mixture to a first predetermined temperature. If heating of the stillage mixture is to be omitted, the stillage mixture may be mixed without heating using mechanical action. The stillage mixture produced by hydroheater 230 may be held in a tank 240 at the desired first predetermined temperature for a first amount of time. Holding the mixed stillage within tank 240 at the first temperature for the first amount of time may permit the physical and chemical separation of the valuable components of the stillage to commence. After the desired first amount of time has elapsed, the mixture may be transferred from tank 240 to a cooler 260. Cooler 240 may flash cool the heated and mixed stillage to a second temperature. Cooler 260 may use a vacuum chamber, for example, to rapidly reduce the temperature of the stillage from the first temperature to the second temperature. Vapors 285 may be captured during the cooling process and used to provide heat to other components of the ethanol production system, such as evaporators. After cooling in the cooler 260, the partially processed stillage 253 may be removed from the bottom of the cooler 260 for additional processing in accordance with the present invention.

Figure 3:
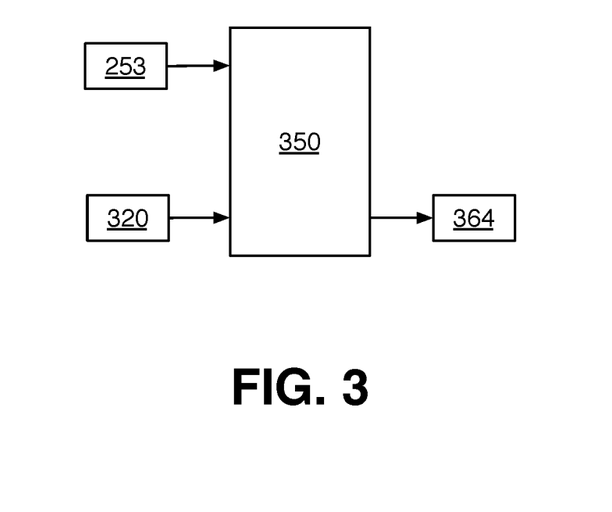
FIG. 3 illustrates an example of a system for the additional treatment of stillage after treatment by the system such as shown in the example of FIG. 2.

Referring now to FIG. 3, an example of a system 300 for the additional treatment of stillage 253 removed from cooler 260 in the example of FIG. 2 in accordance with the present invention is illustrated. An enzymatic treatment may be applied to the partially processed stillage 253 for processing in a reactor 350. An enzyme 320 such as alpha amylase may be used to treat the partially processed stillage 253, although other types of treatments may be used. The enzymatically treated mixture may be retained in the reactor 350 for a predetermined period of time, such as one or more hours. In some examples a residence time of approximately one and a half hours may be used. The residence time may be selected to be sufficient to further breakdown the stillage materials by converting remaining starches into dissolved dextrins. The residence time may vary based upon the temperature of the enzymatically treated stillage and/or the nature of the stillage and the enzymatic treatment itself. Eventually, the enzymatically treated stillage may be removed from the reactor 350 as reactor discharge 364 for additional processing. In some examples in accordance with the present invention, the enzymatic treatment system 300 may be omitted without departing from the scope of the present invention.

Figure 4:
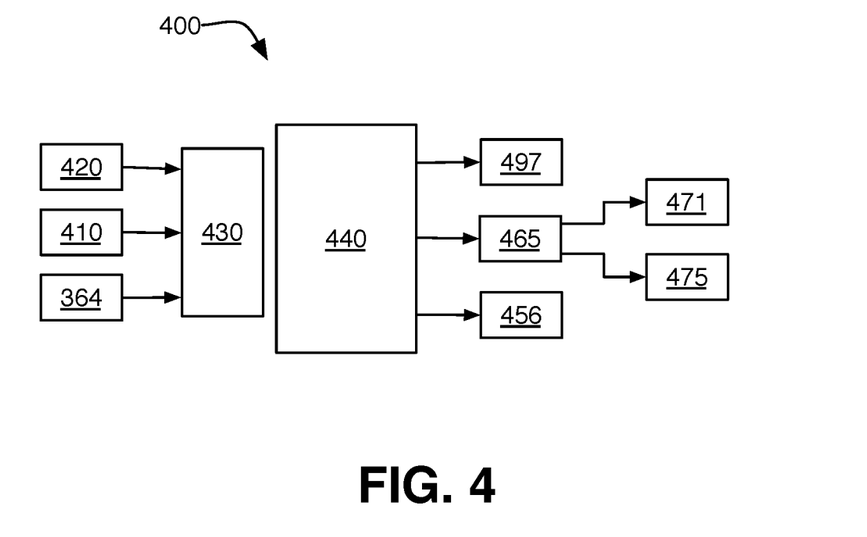
FIG. 4 illustrates an example of a system for the additional treatment of stillage after treatment by the system such as shown in the example of FIG. 3.

Referring now to FIG. 4, the partially processed stillage removed from the reactor 350 of the example of FIG. 3 as reactor discharge 364 may be mixed with water 420 and vegetable oil 410 using a high shear mixing device 430 to form an emulsion. If the enzymatic treatment system 300 of FIG. 3 is omitted, the system 400 depicted in FIG. 4 may receive colled stillage from the system 200 depicted in the example of FIG. 2, or from any other source. The high shear mixing device 430 may comprise, for example, a hydroheater that violently mixes the stillage, oil, and water using high velocity steam forced through a narrow opening. In other examples, mixing device 430 may utilize air or another fluid to generate a shear sufficient to form an emulsion. Mixing device 430 may comprise any other type of the device, system, or process that creates an emulsion from the reactor discharge 364 (which comprises the stillage treated with alpha amylase or other enzymes), oil 410, and/or water 420. The resulting emulsion may be placed in a settling tank 440 for a period of time to permit the components of the emulsion to separate into layers based upon their relative density.

Settling tank 440 may retain the emulsion for an hour or more to permit the physical separation of the components of the emulsion, although a shorter or longer settling time may be used in accordance with the present invention. Settling may permit the physical separation of components of the mixture into layers based upon the relative density of those components. In the present example, a top layer 497, a middle layer 465, and a bottom layer 456 may be separated, but more or fewer layers may be separated in accordance with the present invention. A top layer 497 may be decanted after a period of time for additional processing. The top layer 497 may comprise an emulsion of vegetable oil, protein, and/or water. In some examples, the top layer may be treated after being withdrawn by using directly injected steam to bring the temperature of the top layer of the emulsion up to 200 degrees Fahrenheit. The heated material may be mixed with one or more chemical to assist in breaking the emulsion and the material may be fed to a centrifuge. A relatively clean vegetable oil stream may be collected off of the centrifuge. The protein and water separated from the vegetable oil may be collected and further processed to produce a concentrated protein product. A bottom layer 456 may be removed from the settling tank 440. Bottom layer 456 may comprise fiber that may be processed further. A washing process may wash residual materials off of the fibers contained in the bottom layer to leave a relatively clean fiber stream. A middle layer 465 of dissolved solids may be removed as well. A portion of the dissolved solids 465 may be separated 471 for recycled use while a second portion 475 may be subjected to further processing, some examples of which are described herein.

Figure 5:
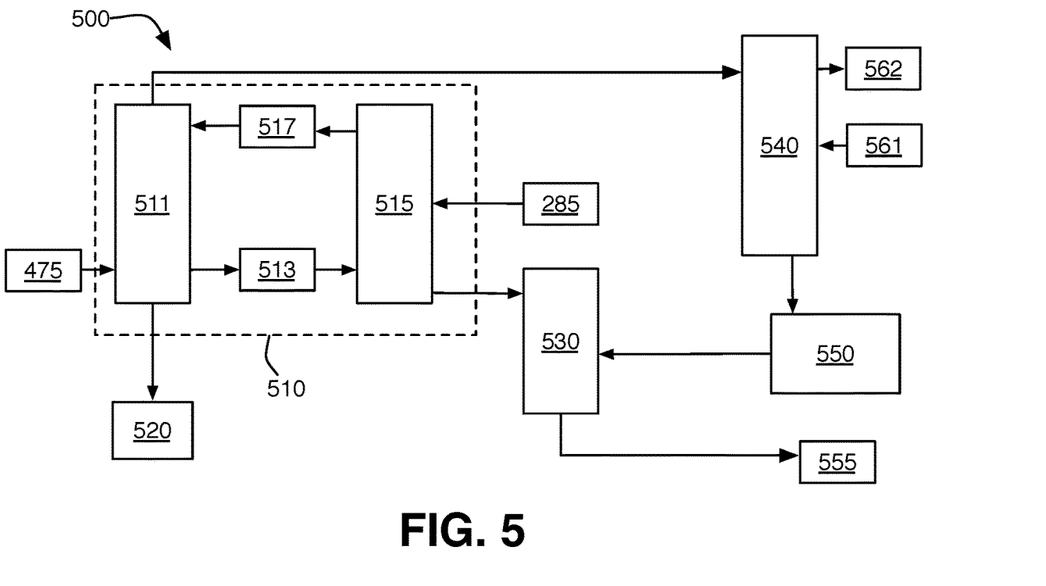
FIG. 5 illustrates an example of a system for the additional treatment of the dissolved solids that may be recovered from a settled emulsification such as may be formed using the exemplary system of FIG. 4.

Referring now to FIG. 5, an example of a system 500 for the additional treatment of the dissolved solids 475 that may be recovered from a settled emulsification such as may be formed using the exemplary system 400 of FIG. 4 is illustrated. Dissolved solids 475 may comprise solids dissolved in water. One or more evaporation system 510 may be used to remove vapors from the dissolved solids and to extract the solids 520 from the dissolved solids 475. In the example of FIG. 5, an evaporation system 510 comprises a heat exchanger 515 and a liquid/vapor separator 511 to separate vapor 513 from liquid 517. Flash vapors 285 obtained during cooling of mixed stillage described above with regard to FIG. 2 may be used to heat the evaporator system 510, although other heat sources may be used. The remaining solids 520 may be separated for use, sale, and/or additional processing. Vapors may be removed from an evaporation system 510 to a condenser 540. Condenser 540 may receive cooling water 561 (and warmed water 562 may be exit condenser 540 for cooling and reuse) to create condensed vapors 550. Other condensed vapors 530 may be collected from an evaporation system 510 and combined with condensed vapors 550 from condenser 540 as a condensate 555 to be output for further use or processing. While the example of FIG. 5 illustrates a single evaporation system 510, systems and methods in accordance with the present invention may provide multiple evaporation systems 510. In other words, multiple evaporation iterations may be performed upon the dissolved solids 475 in order to reach a desired level of purity in processing the material to extract the fullest possible value from the dissolved solids 475. Further, the present invention may use evaporation systems that differ from the system 510 illustrated in the example of FIG. 5.

Figure 6:
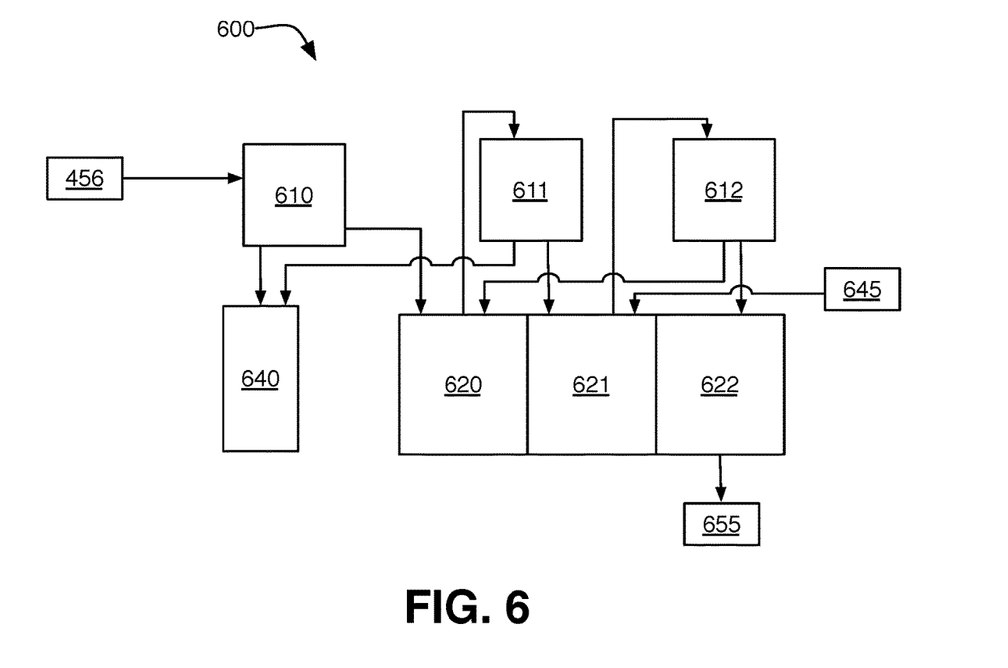
FIG. 6 illustrates an example of a system for the additional treatment of the fiber that may be recovered from a settled emulsification such as may be formed using the exemplary system of FIG. 4.

Referring now to FIG. 6, an example of a system 600 for further processing of fiber 456 removed from the settling tank 440 illustrated in the example of FIG. 4 is shown. A counter flow multiple stage wash process may be used to clean the fiber 456 collected from the bottom layer of the settling tank. The fiber 456 may be washed upon a first screen 640 using wash water 645. Subsequent screens may be iteratively used to remove impurities from the fiber 456. For example, a plurality of screen systems 620, 621, 622 may be used to iteratively process the fiber 456 using wash water 645. The wash water 640, 645 used in the fiber washing system depicted in FIG. 6 may be reclaimed from other steps and components of the systems and methods described herein.

Figure 7:
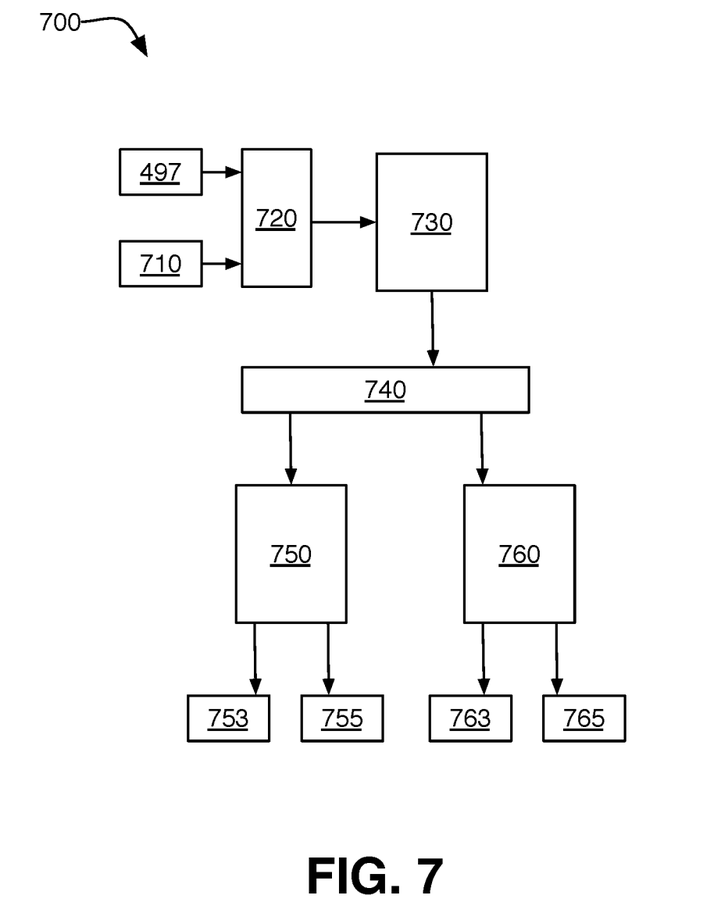
FIG. 7 illustrates an example of a system for the additional treatment of the oil, protein, and water that may be recovered from a settled emulsification such as may be formed using the exemplary system of FIG. 4.

FIG. 7 illustrates an example of a system 700 that may be used for the further treatment of the oil, protein, and water mixture 497 removed from the top of settling tank 440 such as illustrated in the example of FIG. 4. The oil, protein, and water mixture 497 may be mixed with steam 710 using a mixing device 720, such as a hydroheater, and may be further mixed with additional chemical treatments and held in a treatment tank 730 at a desired temperature for a desired period of time. For example, treatment tank 730 may hold the heated mixture for a period of time at approximately 200° F. After permitting sufficient time for a chemical treatment to facilitate the separation of the materials in the mixture 497, a centrifuge 740 may separate the solids 750 from the oil 760. While the entirety of the solids 750 and/or the entirety of the oil 760 may thereafter be further processed, sold, or used for other commercial purposes, it is also possible to separate each into multiple streams, at least some of which may be recycled for use elsewhere in the systems and methods in accordance with the present invention. For example, the solids 750 may be split into a first solid stream 753 and a second solid stream 755. Similarly, the oil 760 may be split into a first oil stream 763 and a second oil stream 765. For example, the first oil stream 763 may provide a sufficient amount of vegetable oil for use in creating an emulsion such as depicted and described in conjunction with FIG. 4.

Figure 8:
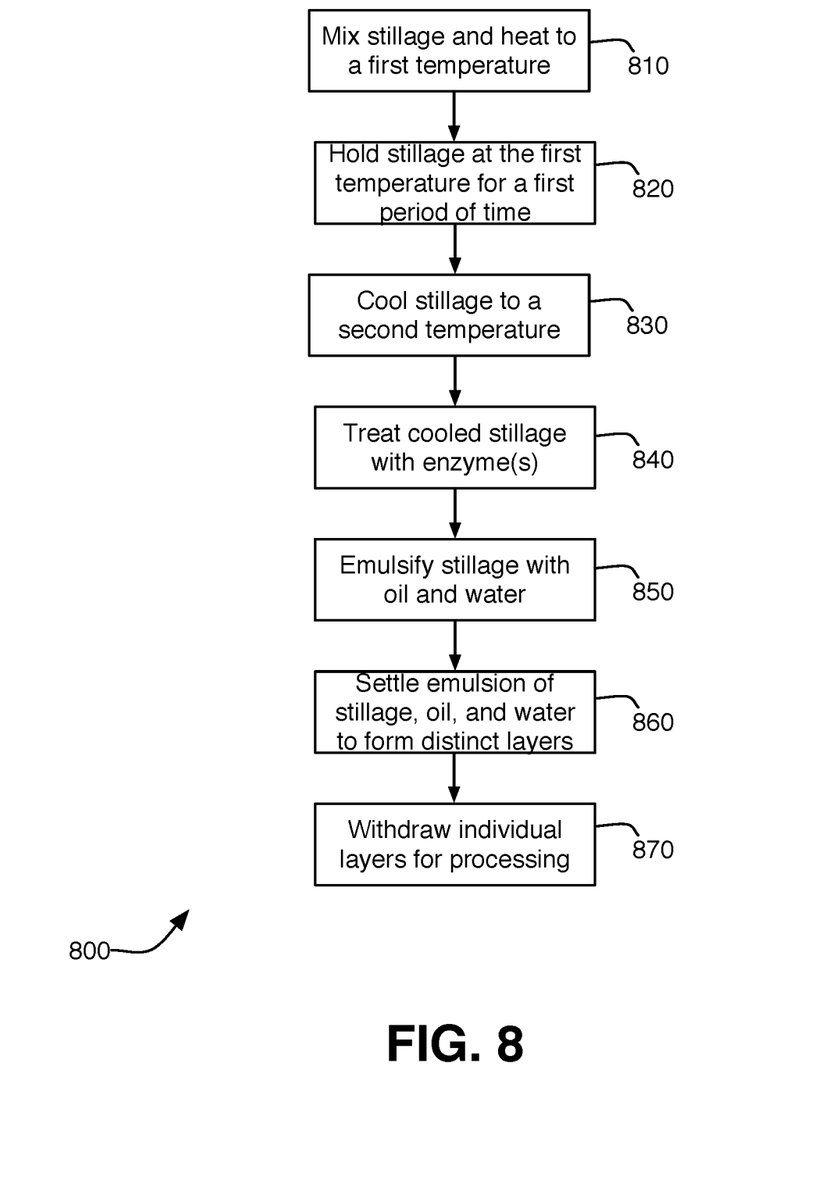
FIG. 8 illustrates a further example of a method in accordance with the present invention.

FIG. 8 illustrates a further example of a method 800 in accordance with the present invention. In step 810 stillage remaining after the fermentation process has completed may be mixed and heated to a first temperature. In some examples, step 810 may be performed using a hydroheater to both heat and mix the stillage at the same time. The first temperature may be 250 degrees Fahrenheit. In further examples, step 810 may only mix the stillage, or may be omitted entirely. In step 820 the stillage may be held at the first temperature for a first period of time. In some examples, the first period of time may be five minutes. Step 820 may be omitted if step 810 is omitted or does not heat the stillage. In step 830 the stillage may be cooled to a second temperature. In some examples the second temperature may be 185 degrees Fahrenheit. Step 830 may be performed using a vacuum chamber to flash cool the stillage. Vapors may be captured during cooling step 830 and reused elsewhere in an ethanol production facility. Step 830 may be omitted if the stillage is not heated in step 810. In step 840 the cooled stillage may be treated with enzyme(s) to facilitate the chemical and physical breakdown of the stillage. In some examples, the enzyme used in step 840 may be alpha amylase. Step 840 may be performed in a reaction vessel that retains the enzymatically treated stillage at a desired temperature for a period of time while the treatment occurs. For example, in step 840 the enzymatically treated stillage may be retained for at least one and a half hours. In some examples, enzymatic treatment step 840 may be omitted, and method 800 may proceed to step 850. In step 850 the stillage may be emulsified with oil and water. Step 850 may use a high shear mixer, such as a hydroheater, to combine the stillage with oil and water to form an emulsion. The oil used in step 850 may be a vegetable oil reclaimed from stillage using method 800. In step 860 the emulsion of stillage, oil, and water may be allowed to settle for a sufficient period of time to permit distinct layers to form. In some examples, step 860 may permit the emulsion of stillage, oil, and water to settle for one and a half hours or more. In step 870 individual layers that have been formed in the emulsion may be individually withdrawn. After step 870, additional methods or processing may be performed on one or more withdrawn layer to isolate and/or concentrate the materials that aggregated in the layer. Step 870 may withdraw a bottom layer containing fiber, a middle layer containing dissolved solids, and a top layer containing oil and protein. After The present invention provides systems and methods that enable the valuable components of the stillage remaining after grain-based ethanol production to be separated and isolated for further sale or other use. In this fashion, the economic viability of ethanol production may be increased and the waste associated with ethanol production may be drastically reduced. As a result, the environmental benefit of ethanol as a fuel source is enhanced, and the profitability of ethanol distillation is increased. Systems and methods in accordance with the present invention are not limited to any particular type of ethanol production, any particular type of grain input, or any particular use of the products isolated in accordance with the present invention.

Systems and methods in accordance with the present invention may separate the components of stillage for processing by creating an emulsion of the stillage, for example through high-shear mixing with oil and water, and permitting the components of the resulting emulsion to settle into layers based upon density. Prior to forming the emulsion, the stillage may be treated to facilitate the physical and/or chemical breakdown of the stillage. Stillage may be treated through heating, mixing, cooling, enzymatic treatment, and/or chemical treatment. One or more layer may be removed from the settled emulsion for further processing. Layers may separated by permitting the emulsion to settle. The layers formed by permitting an emulsion to settle may comprise a top layer of vegetable oil, protein, and water; a middle layer of dissolved solids; and a bottom layer of fiber. However, more or fewer layers may be separated for additional processing using systems and methods in accordance with the present invention. A variety of processes, systems, and/or methods may be used to process, further separate, and/or purify the material collected from layers of the settled emulsion. In some examples, evaporation, washing, chemical treatment, heating, centrifuges, and similar approaches may be used to isolate one or more substance that was contained in the stillage.

The invention claimed is:

1. A system for separating stillage after the fermentation process of ethanol production has concluded, the system comprising:
   (a) a high shear mixer that combines stillage from an ethanol fermenter with water and oil to create an emulsion;
   (b) a settling tank that receives the emulsion and retains the emulsion for a predetermined period of time, thereby permitting components of the emulsion to separate into discrete layers; and
   (c) at least one extraction mechanism that draws individual layers from the settling tank for further processing.

2. The system of claim 1, further comprising a reaction vessel that treats the stillage with an enzyme before the stillage is transferred to the high shear mixer.

3. The system of claim 2, wherein the enzyme used to treat the stillage comprises alpha amylase.

4. The system of claim 3, wherein the high shear mixer comprises a hydroheater that forces the stillage through an opening with the water and oil.

5. The system of claim 4, wherein the at least one extraction mechanism withdraws at least a bottom layer containing fibers, a middle layer containing dissolved solids, and a top layer containing proteins and oil.

6. The system of claim 5, wherein the oil used to create the emulsion comprises vegetable oil recycled from the top layer.

7. The system of claim 6, further comprising at least one distinct system to process each of the discrete layers.

8. A system for separating stillage after the fermentation process of ethanol production has concluded, the system comprising:
   (a) a vessel that receives spent stillage, mixes the spent stillage, and heats the spent stillage to a first predetermined temperature;
   (b) a cooling chamber that rapidly cools the spent stillage after the spent stillage has been heated to the first predetermined temperature by the vessel;
   (c) an enzymatic treatment system that adds an enzyme to the spent stillage after it has been cooled in the cooling chamber;
   (d) an emulsifier that mixes the spent stillage and the enzyme with oil and water to create an emulsion;
   (e) a settling tank that receives the emulsion and retains the emulsion for a predetermined period of time to permit the emulsion to separate into layers; and
   (f) at least one system that processes at least one layer formed while the emulsion is held in the settling tank.

9. The system of claim 8, wherein the enzymatic treatment system comprises a reaction vessel that holds stillage for between one hour and two hours after treating the stillage with alpha amylase.

10. The system of claim 9, wherein the emulsifier comprises a hydroheater that forces the spent stillage, oil, and water through an opening with high shear force.

11. The system of claim 10, wherein the vessel that receives spent stillage, mixes the spent stillage, and heats the spent stillage to a first predetermined temperature further retains the spent stillage at the first predetermined temperature for a first predetermined period of time.

12. The system of claim 11, wherein the settling tank that receives the emulsion and retains the emulsion for a predetermined period of time to permit the emulsion to separate into layers retains the emulsion for at least one hour.

* * * * *